(12) United States Patent
Cao et al.

(10) Patent No.: US 11,948,285 B2
(45) Date of Patent: Apr. 2, 2024

(54) IMAGING SYSTEMS WITH MULTIPLE RADIATION SOURCES

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 251 days.

(21) Appl. No.: 17/368,402

(22) Filed: Jul. 6, 2021

(65) Prior Publication Data
US 2023/0010044 A1    Jan. 12, 2023

(51) Int. Cl.
*G06K 9/00* (2022.01)
*G06T 3/4038* (2024.01)
*G06T 5/50* (2006.01)

(52) U.S. Cl.
CPC .............. *G06T 5/50* (2013.01); *G06T 3/4038* (2013.01); *G06T 2207/10116* (2013.01); *G06T 2207/20221* (2013.01)

(58) Field of Classification Search
CPC . G06T 5/50; G06T 2207/20221; G06T 15/00; G06T 17/00; G06T 11/005; G06T 3/4038; G06T 2207/10116; A61B 6/5241; A61B 6/032; A61B 6/4233; A61B 6/4266; H04N 5/32; H01L 31/00; G01N 2223/079; G01N 23/04; G01T 1/24; G01T 1/2018; G01T 1/20181; G01T 1/20182; G01T 1/242; G01J 3/2823
See application file for complete search history.

(56) References Cited

U.S. PATENT DOCUMENTS

| | | | |
|---|---|---|---|
| 6,272,207 B1* | 8/2001 | Tang | G21K 1/025 378/154 |
| 2016/0123902 A1* | 5/2016 | Lowell | H01J 35/04 378/62 |
| 2016/0270745 A1* | 9/2016 | Heath | A61B 6/4007 |
| 2018/0350112 A1* | 12/2018 | Wang | G06T 11/006 |
| 2019/0069858 A1* | 3/2019 | Cao | A61B 6/5241 |

OTHER PUBLICATIONS

Borisova,E., Lovric, G.,Miettinen, A.,Fardin, L.,Bayat, S.,Larsson, A.,Stampanoni, M.,Schittny, J. C., & Schlepütz, C. M. (2021). Micrometer-resolution X-ray tomographic full-volume reconstruction of an intact post-mortem juvenile rat lung. Histochemistry and cell biology, 155(2), 215-226. http (Year: 2020).*

* cited by examiner

*Primary Examiner* — Emily C Terrell
*Assistant Examiner* — Kevin M Coomber
(74) *Attorney, Agent, or Firm* — IPRO, PLLC; Qian Gu (57) ABSTRACT

Disclosed herein is a method and a system for reconstructing a three-dimensional image of an object, based on stitched images of the object obtained using multiple beams.

26 Claims, 9 Drawing Sheets

IMAGING SYSTEMS WITH MULTIPLE RADIATION SOURCES

BACKGROUND

A radiation detector is a device that measures a property of a radiation. Examples of the property may include a spatial distribution of the intensity, phase, and polarization of the radiation. The radiation measured by the radiation detector may be a radiation that has transmitted through an object. The radiation measured by the radiation detector may be an electromagnetic radiation such as infrared light, visible light, ultraviolet light, X-ray, or y-ray. The radiation may be of other types such as α-rays and β-rays. An imaging system may include one or more image sensors each of which may have one or more radiation detectors.

SUMMARY

Disclosed herein is a method, comprising: for i=1, ..., M, and j=1, ..., Ni, sending a beam group (i, j) toward a same object and then toward a same image sensor; for each value of i and each value of j, capturing with the image sensor a partial image (i, j) of the object using radiation of the beam group (i, j) that has transmitted through the object; for each value of i, stitching the partial images (i, j), j=1, ..., Ni resulting in a stitched image (i) of the object; and reconstructing a three-dimensional image of the object based on the stitched images (i), i=1, ..., M, wherein the beam groups (i, j), i=1, ..., M, and j32 1, ..., Ni are sent one beam group at a time, wherein the image sensor comprises P active areas, wherein for each value of i and each value of j, the beam group (i, j) comprises P radiation beams sent simultaneously and aimed respectively at the P active areas, wherein M and Ni, i=1, ..., M are integers greater than 1, and wherein P is a positive integer.

In an aspect, for each value of i and each value of j, no ray of the beam group (i, j) is aimed at outside the P active areas.

In an aspect, P>1.

In an aspect, for each value of i, each point of the object is in at least a partial image of the partial images (i, j), j=1, ..., Ni.

In an aspect, the beam groups (i, j), i=1, ..., M, and j=1, ..., Ni are sent from a mask; for each value of i, the beam groups (i, j), j=1, ..., Ni are sent from a window group (i) of the mask; for each value of i, the window group (i) comprises P windows, and for each value of i and each value of j, the P radiation beams of the beam group (i, j) are sent from respectively the P windows of the window group (i).

In an aspect, the mask has a shape of a plate; a pixel plane intersects all sensing elements of the image sensor; and the mask is parallel to the pixel plane when each partial image of the partial images (i, j), i=1, ..., M, and j=1, ..., Ni is captured.

In an aspect, the pixel plane and the mask is of a same distance apart when each partial image of the partial images (i, j), i=1, ..., M, and j=1, ..., Ni is captured.

In an aspect, for each value of i, the mask is moved in a scanning direction through Ni mask positions, and for each value of i, the partial images (i, j), j=1, ..., Ni are captured when the mask is at the Ni mask positions respectively.

In an aspect, for each value of i, the image sensor is moved in the scanning direction through Ni image sensor positions, and for each value of i, the partial images (i, j), j=1, ..., Ni are captured when the image sensor is at the Ni image sensor positions respectively.

In an aspect, at least a pair of q and r are of 1, ..., M, q≠r, at least a pair of s and t are of 1, ..., Nq and 1, ..., Nr respectively, a position of the mask when the partial image (q, s) is captured and a position of the mask when the partial image (r, t) is captured are the same, and a position of the image sensor when the partial image (q, s) is captured and a position of the image sensor when the partial image (r, t) is captured are the same.

In an aspect, for each value of i, all rays of the beam groups (i, j), j=1, ..., Ni come from a point (i), and for each value of i and each value of j, each radiation beam of the beam group (i, j) is a truncated pyramid beam.

In an aspect, for each value of i and each value of j, no ray is part of at least two radiation beams of the P radiation beams of the beam group (i, j).

In an aspect, the points (i), i=1, ..., M and the object are stationary with respect to each other, and said capturing comprises moving the image sensor with respect to the object.

In an aspect, the points (i), i=1, ..., M are on a straight line parallel to a pixel plane that intersects all sensing elements of the image sensor.

In an aspect, for each value of i, said sending the beam groups (i, j), j=1, ..., Ni comprises bombarding a same metal target region at the point (i) with electron beams.

In an aspect, for each value of i and each value of j, each radiation beam of the P radiation beams of the beam group (i, j) comprises X-rays.

Disclosed herein is a system, comprising: an image sensor, wherein the system is configured to, for i=1, ..., M, and j=1, ..., Ni, send a beam group (i, j) through a same object and then toward the image sensor, wherein the image sensor is configured to, for each value of i and each value of j, capture a partial image (i, j) of the object using radiation of the beam group (i, j) that has transmitted through the object, wherein the system is configured to, for each value of i, stitch the partial images (i, j), j=1, ..., Ni resulting in a stitched image (i) of the object, wherein the system is configured to reconstruct a three-dimensional image of the object based on the stitched images (i), i=1, ..., M, wherein the beam groups (i, j), i=1, ..., M, and j=1, ..., Ni are sent one beam group at a time, wherein the image sensor comprises P active areas, wherein for each value of i and each value of j, the beam group (i, j) comprises P radiation beams sent simultaneously and aimed respectively at the P active areas, wherein M and Ni, i=1, ..., M are integers greater than 1, and wherein P is a positive integer.

In an aspect, for each value of i and each value of j, no ray of the beam group (i, j) is aimed at outside the P active areas.

In an aspect, P>1.

In an aspect, for each value of i, each point of the object is in at least a partial image of the partial images (i, j), j=1, ..., Ni.

In an aspect, the system further comprises a mask. The beam groups (i, j), i=1, ..., M, and j=1, ..., Ni are sent from the mask; for each value of i, the beam groups (i, j), j=1, ..., Ni are sent from a window group (i) of the mask; for each value of i, the window group (i) comprises P windows; and for each value of i and each value of j, the P radiation beams of the beam group (i, j) are sent from respectively the P windows of the window group (i).

In an aspect, the mask has a shape of a plate; a pixel plane intersects all sensing elements of the image sensor; and the mask is parallel to the pixel plane when each partial image of the partial images (i, j), i=1, ..., M, and j=1, ..., Ni is captured.

In an aspect, the pixel plane and the mask is of a same distance apart when each partial image of the partial images (i, j), i=1, . . . , M, and j=1, . . . , Ni is captured.

In an aspect, for each value of i, the mask is configured to move in a scanning direction through Ni mask positions, and for each value of i, the partial images (i, j), j=1, . . . , Ni are captured when the mask is at the Ni mask positions respectively.

In an aspect, for each value of i, the image sensor is configured to move in the scanning direction through Ni image sensor positions, and for each value of i, the partial images (i, j), j=1, . . . , Ni are captured when the image sensor is at the Ni image sensor positions respectively.

In an aspect, at least a pair of q and r are of 1, . . . , M; q≠r; at least a pair of s and t are of 1, . . . , Nq and 1, . . . , Nr respectively; a position of the mask when the partial image (q, s) is captured and a position of the mask when the partial image (r, t) is captured are the same, and a position of the image sensor when the partial image (q, s) is captured and a position of the image sensor when the partial image (r, t) is captured are the same.

In an aspect, for each value of i, all rays of the beam groups (i, j), j=1, . . . , Ni come from a point (i), and for each value of i and each value of j, each radiation beam of the beam group (i, j) is a truncated pyramid beam.

In an aspect, for each value of i and each value of j, no ray is part of at least two radiation beams of the P radiation beams of the beam group (i, j).

In an aspect, the points (i), i=1, . . . , M and the object are stationary with respect to each other, and the image sensor is configured to move with respect to the object.

In an aspect, the points (i), i=1, . . . , M are on a straight line parallel to a pixel plane that intersects all sensing elements of the image sensor.

In an aspect, the system is configured to, for each value of i, bombard a metal target region at the point (i) with electron beams.

In an aspect, for each value of i and each value of j, each radiation beam of the P radiation beams of the beam group (i, j) comprises X-rays.

DETAILED DESCRIPTION

Radiation Detector

Figure 1:
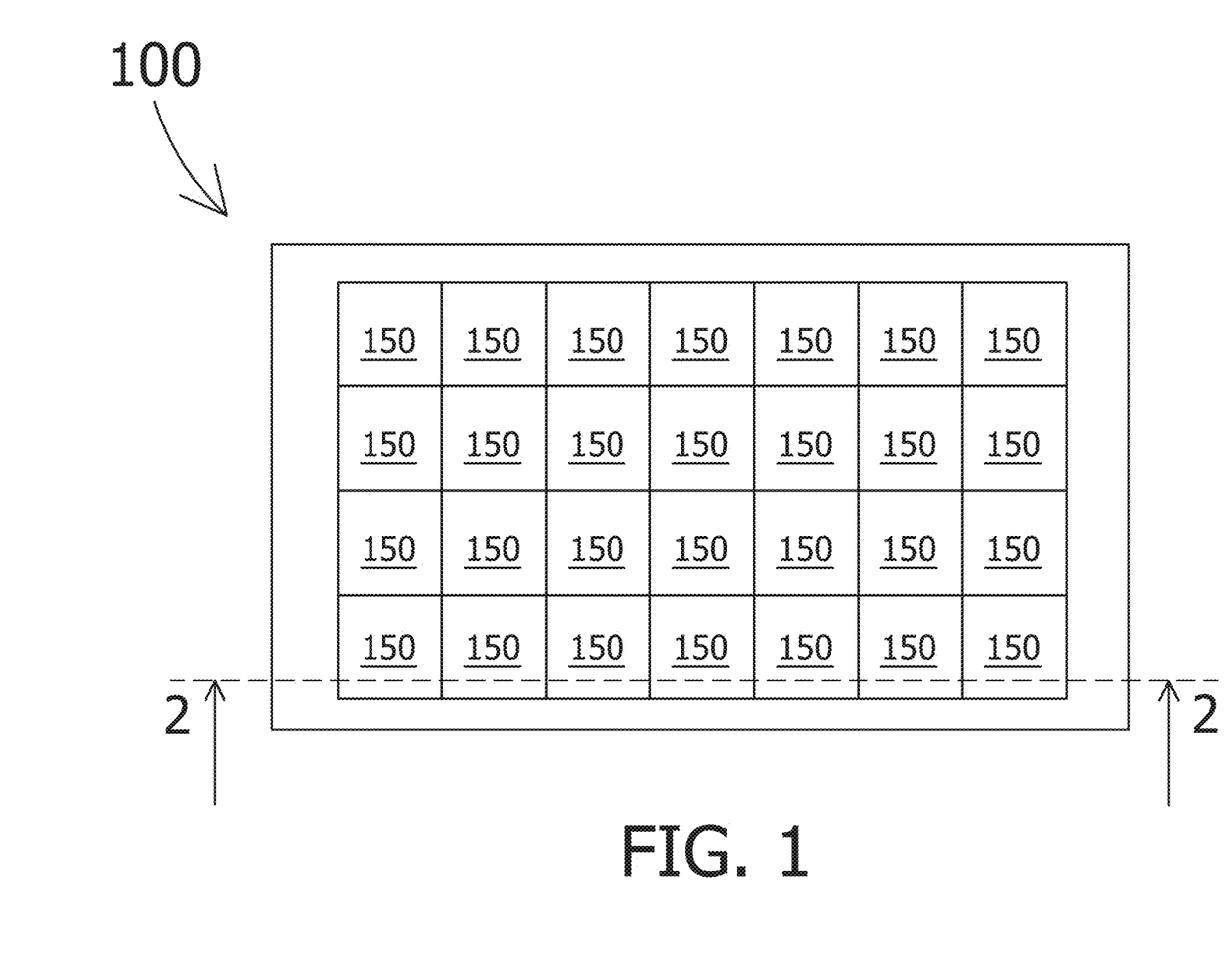
FIG. 1 schematically shows a radiation detector, according to an embodiment.

FIG. 1 schematically shows a radiation detector 100, as an example. The radiation detector 100 may include an array of pixels 150 (also referred to as sensing elements 150). The array may be a rectangular array (as shown in FIG. 1), a honeycomb array, a hexagonal array, or any other suitable array. The array of pixels 150 in the example of FIG. 1 has 4 rows and 7 columns; however, in general, the array of pixels 150 may have any number of rows and any number of columns.

Each pixel 150 may be configured to detect radiation from a radiation source (not shown) incident thereon and may be configured to measure a characteristic (e.g., the energy of the particles, the wavelength, and the frequency) of the radiation. A radiation may include particles such as photons and subatomic particles. Each pixel 150 may be configured to count numbers of particles of radiation incident thereon whose energy falls in a plurality of bins of energy, within a period of time. All the pixels 150 may be configured to count the numbers of particles of radiation incident thereon within a plurality of bins of energy within the same period of time. When the incident particles of radiation have similar energy, the pixels 150 may be simply configured to count numbers of particles of radiation incident thereon within a period of time, without measuring the energy of the individual particles of radiation.

Each pixel 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

Figure 2:
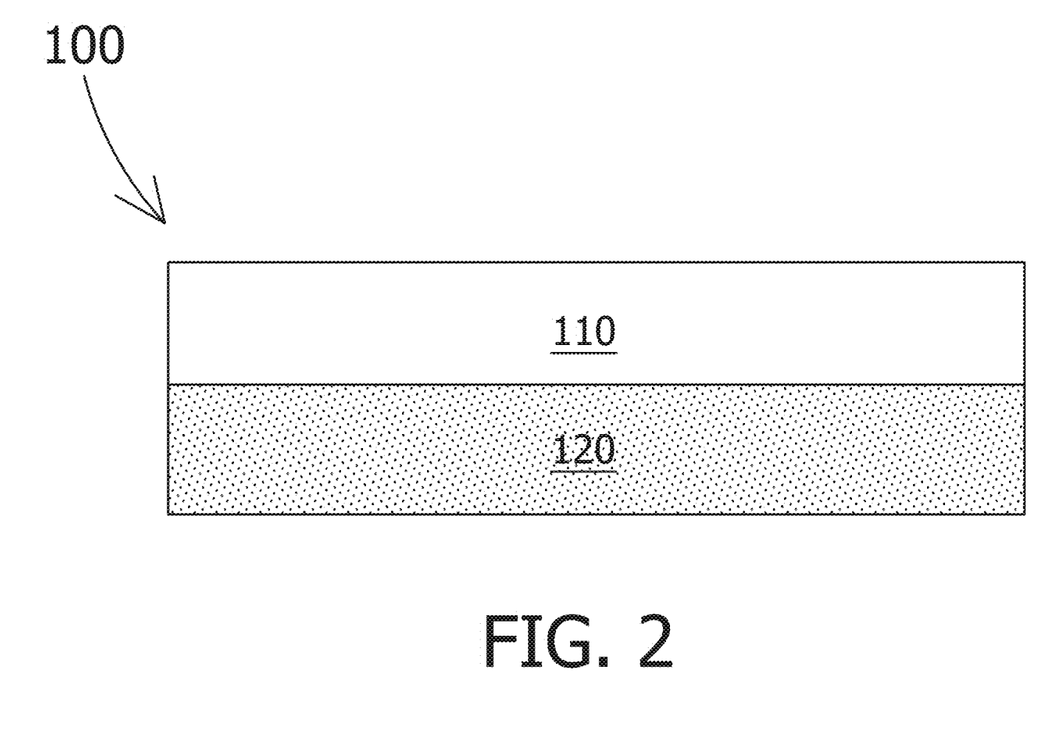
FIG. 2 schematically shows a simplified cross-sectional view of the radiation detector, according to an embodiment.

FIG. 2 schematically shows a simplified cross-sectional view of the radiation detector 100 of FIG. 1 along a line 2-2, according to an embodiment. Specifically, the radiation detector 100 may include a radiation absorption layer 110 and an electronics layer 120 (which may include one or more ASICs or application-specific integrated circuits) for processing or analyzing electrical signals which incident radiation generates in the radiation absorption layer 110. The radiation detector 100 may or may not include a scintillator (not shown). The radiation absorption layer 110 may include a semiconductor material such as silicon, germanium, GaAs, CdTe, CdZnTe, or a combination thereof. The semiconductor material may have a high mass attenuation coefficient for the radiation of interest.

Figure 3:
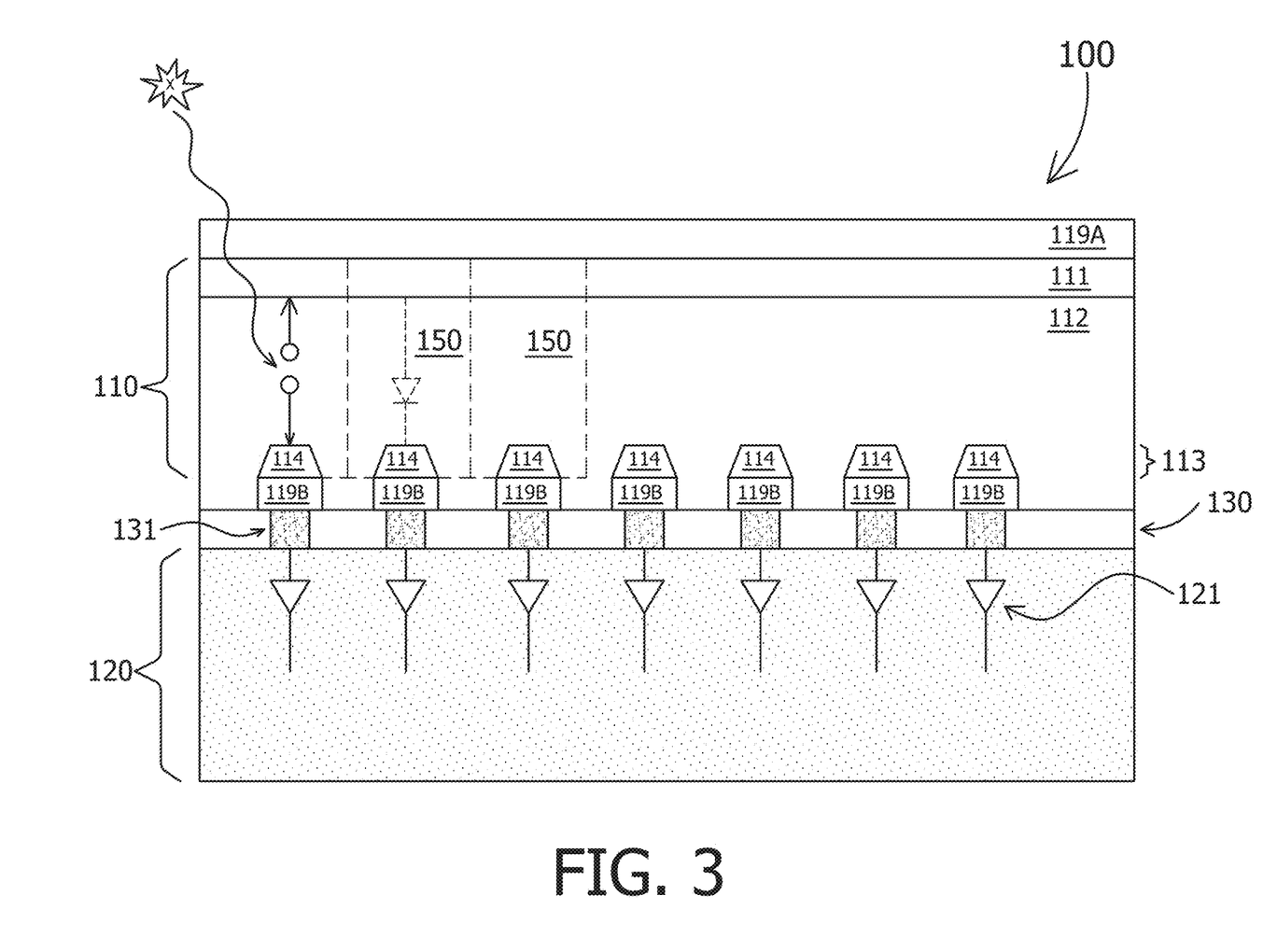
FIG. 3 schematically shows a detailed cross-sectional view of the radiation detector, according to an embodiment.

FIG. 3 schematically shows a detailed cross-sectional view of the radiation detector 100 of FIG. 1 along the line 2-2, as an example. Specifically, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 may be separated from one another by the first doped region 111 or the intrinsic region 112. The first doped region 111 and the second doped region 113 may have opposite types of doping (e.g., region 111 is p-type and region 113 is n-type, or region 111 is n-type and region 113 is p-type). In the example of FIG. 3, each of the discrete regions 114 of the second doped region 113 forms a diode with the first doped region 111 and the optional intrinsic region 112. Namely, in the example in FIG. 3, the radiation absorption layer 110 has a plurality of diodes (more specifically, 7 diodes corresponding to 7 pixels 150 of one row in the array of FIG. 1, of which only 2 pixels 150 are labeled in FIG. 3 for simplicity). The plurality of diodes may have an electrical contact 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs (analog to digital converters). The electronic system 121 may include components shared by the pixels 150 or components dedicated to a single pixel 150. For example, the electronic system 121 may include an amplifier dedicated to each pixel 150 and a microprocessor shared among all the pixels 150. The electronic system 121 may be electrically connected to the pixels 150 by vias 131. Space among the vias may be filled with a filler material 130, which may increase the mechanical stability of the connection of the electronics layer 120 to the radiation absorption layer 110. Other bonding techniques are possible to connect the electronic system 121 to the pixels 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The electric field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 4:
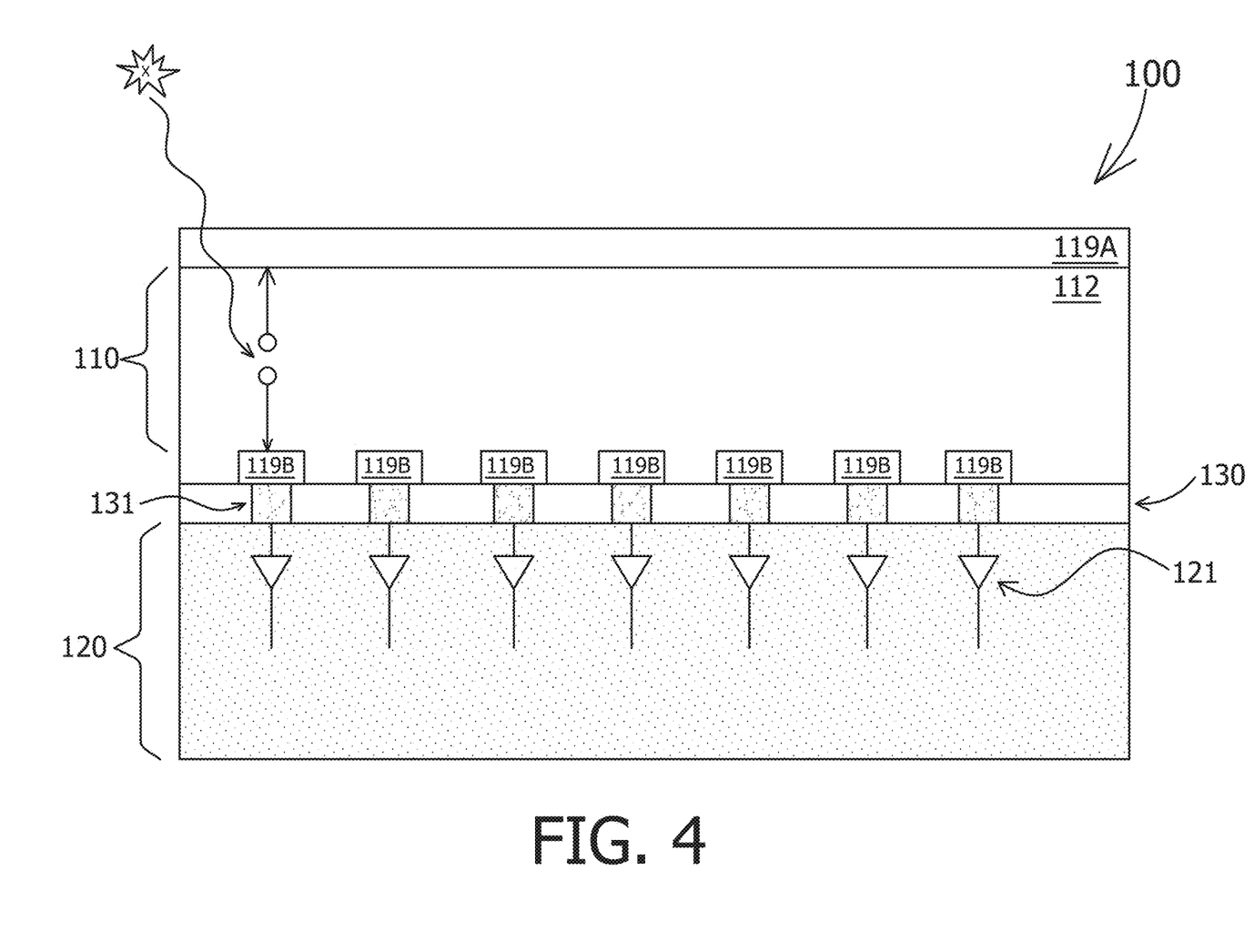
FIG. 4 schematically shows a detailed cross-sectional view of the radiation detector, according to an alternative embodiment.

FIG. 4 schematically shows a detailed cross-sectional view of the radiation detector 100 of FIG. 1 along the line 2-2, according to an alternative embodiment. More specifically, the radiation absorption layer 110 may include a resistor of a semiconductor material such as silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 4 is similar to the electronics layer 120 of FIG. 3 in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B may include discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

Radiation Detector Package

Figure 5:
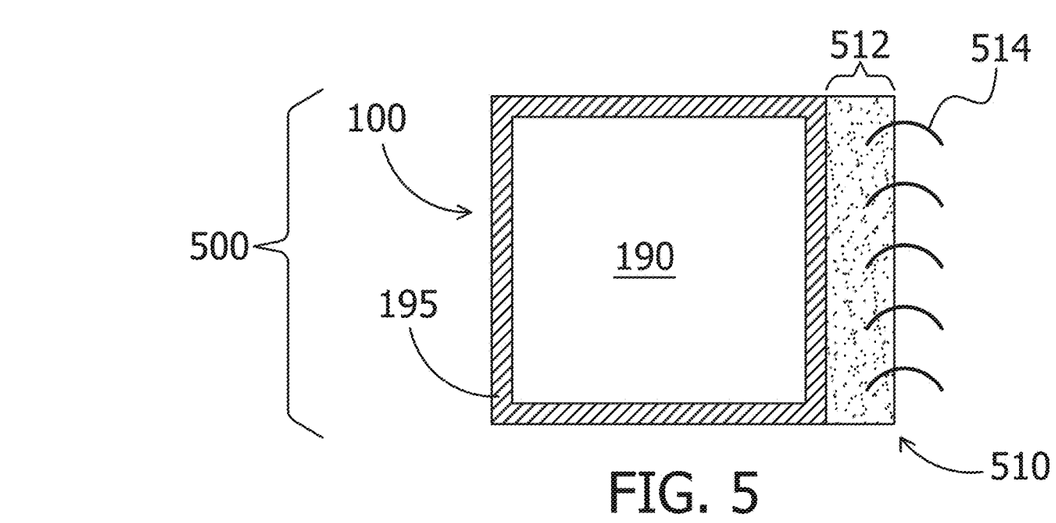
FIG. 5 schematically shows a top view of a package including the radiation detector and a printed circuit board (PCB), according to an embodiment.

FIG. 5 schematically shows a top view of a package 500 including the radiation detector 100 and a printed circuit board (PCB) 510. The term "PCB" as used herein is not limited to a particular material. For example, a PCB may include a semiconductor. The radiation detector 100 may be mounted to the PCB 510. The wiring between the radiation detector 100 and the PCB 510 is not shown for the sake of clarity. The PCB 510 may have one or more radiation detectors 100. The PCB 510 may have an area 512 not covered by the radiation detector 100 (e.g., for accommodating bonding wires 514). The radiation detector 100 may have an active area 190 which is where the pixels 150 (FIG. 1) are located. The radiation detector 100 may have a perimeter zone 195 near the edges of the radiation detector 100. The perimeter zone 195 has no pixels 150, and the radiation detector 100 does not detect particles of radiation incident on the perimeter zone 195.

Image Sensor

Figure 6A:
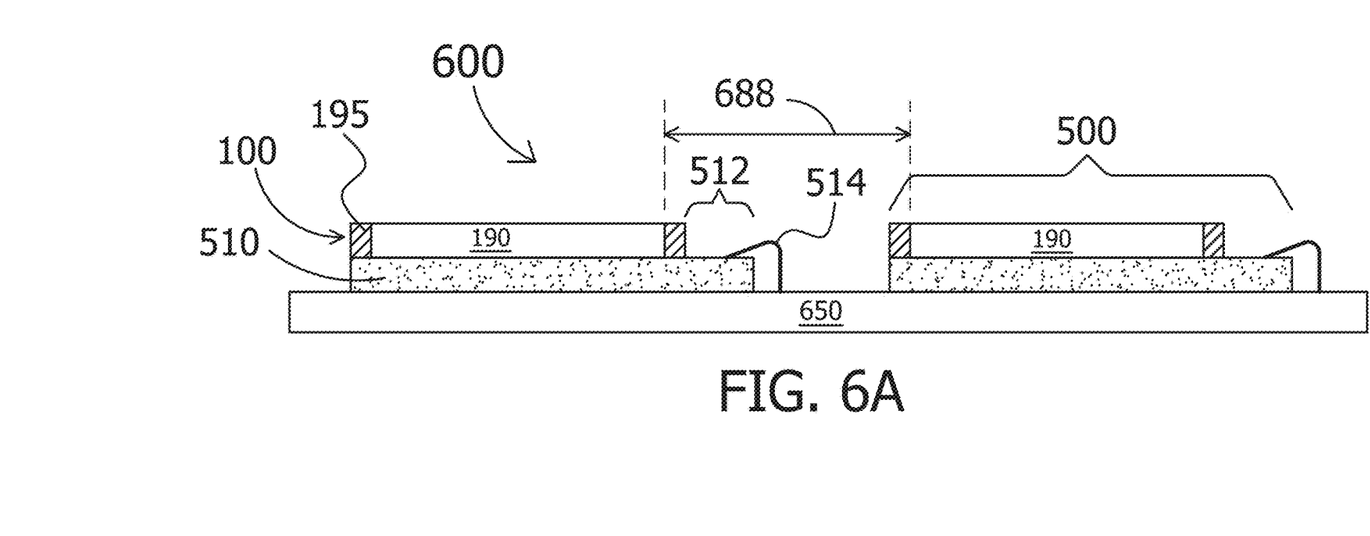
FIG. 6A schematically shows a cross-sectional view of an image sensor including the packages of FIG. 5 mounted to a system PCB (printed circuit board), according to an embodiment.

FIG. 6A schematically shows a cross-sectional view of an image sensor 600, according to an embodiment. The image sensor 600 may include one or more packages 500 of FIG. 5 mounted to a system PCB 650. FIG. 6A shows 2 packages 500 as an example. The electrical connection between the PCBs 510 and the system PCB 650 may be made by bonding wires 514. In order to accommodate the bonding wires 514 on the PCB 510, the PCB 510 may have the area 512 not covered by the radiation detector 100. In order to accommodate the bonding wires 514 on the system PCB 650, the packages 500 may have gaps in between. The gaps may be approximately 1 mm or more. Particles of radiation incident on the perimeter zones 195, on the area 512, or on the gaps cannot be detected by the packages 500 on the system PCB 650. A dead zone of a radiation detector (e.g., the radiation detector 100) is the area of the radiation-receiving surface of the radiation detector, on which incident particles of radiation cannot be detected by the radiation detector. A dead zone of a package (e.g., package 500) is the area of the radiation-receiving surface of the package, on which incident particles of radiation cannot be detected by the radiation detector or detectors in the package. In this example shown in FIG. 5 and FIG. 6A, the dead zone of the package 500 includes the perimeter zones 195 and the area 512. A dead zone (e.g., 688) of an image sensor (e.g., image sensor 600) with a group of packages (e.g., packages 500 mounted on the same PCB and arranged in the same layer or in different layers) includes the combination of the dead zones of the packages in the group and the gaps between the packages.

In an embodiment, the radiation detector 100 (FIG. 1) operating by itself may be considered an image sensor. In an embodiment, the package 500 (FIG. 5) operating by itself may be considered an image sensor.

The image sensor 600 including the radiation detectors 100 may have the dead zone 688 among the active areas 190 of the radiation detectors 100. However, the image sensor 600 may capture multiple partial images of an object or scene (not shown), and then these captured partial images may be stitched to form an image of the entire object or scene.

The term "image" in the present application is not limited to spatial distribution of a property of a radiation (such as intensity). For example, the term "image" may also include the spatial distribution of density of a substance or element.

Figure 6B:
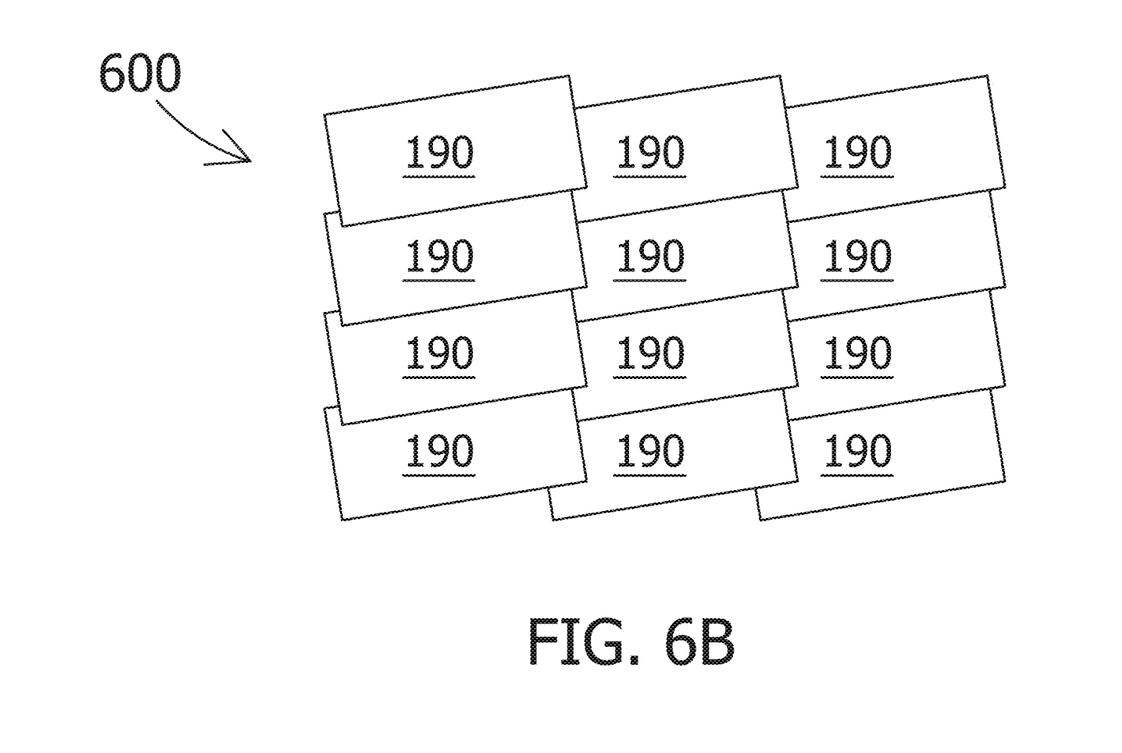
FIG. 6B schematically shows a top view of the image sensor, according to an alternative embodiment.

FIG. 6B schematically shows a top view of the image sensor 600, according to an alternative embodiment. In this alternative embodiment, the image sensor 600 may include multiple radiation detectors 100 arranged in an overlapping manner such that there is no dead zone 688 (FIG. 6A) among the active areas 190 of the radiation detectors 100. For simplicity, only the active areas 190 of the radiation detectors 100 are shown in FIG. 6B.

Imaging Process

Initial System Arrangement

Figure 7:
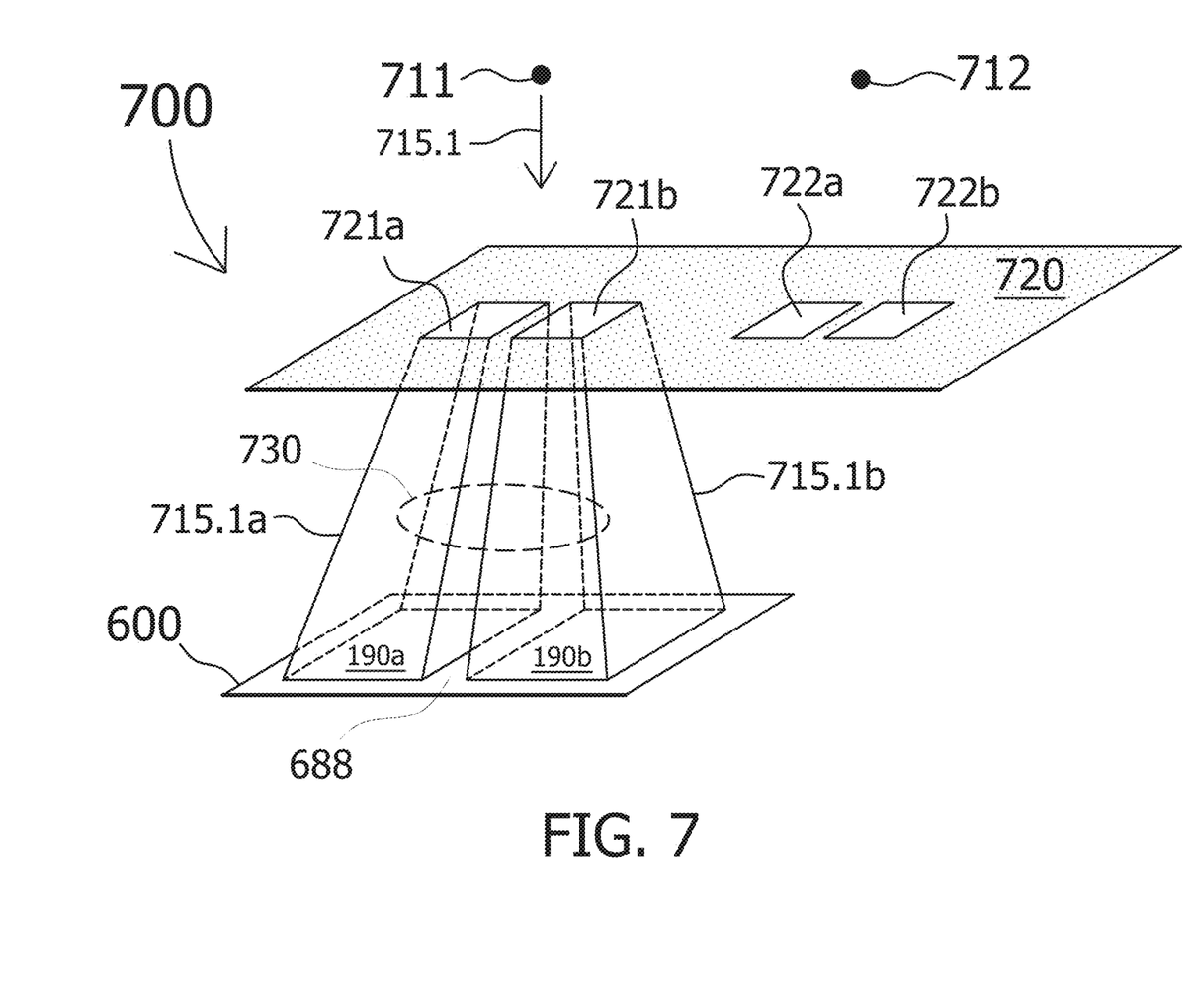
FIGS. 7, 8A-8B, 9A-9B and 10A-10B schematically show an imaging system in operation, according to an embodiment.

FIG. 7 schematically shows a perspective view of an imaging system 700, according to an embodiment. Specifically, the imaging system 700 may include radiation sources 711 and 712, a mask 720, and the image sensor 600.

In an embodiment, the radiation sources 711 and 712 may generate radiation beams (e.g., X-rays) toward the mask 720.

In an embodiment, the mask 720 may include 2 window groups 721a+721b and 722a+722b. The window group 721a+721b may include 2 windows 721a and 721b. The window group 722a+722b may include 2 windows 722a and 722b. In an embodiment, the radiation particles from the radiation sources 711 and 712 and incident on the windows of the mask 720 are allowed to transmit through the mask 720, whereas the radiation particles from the radiation sources 711 and 712 and incident on the other regions of the mask 720 are blocked. In an embodiment, the mask 720 may have the shape of a plate as shown.

In an embodiment, the image sensor 600 may include 2 radiation detectors 100 that include 2 active areas 190a and 190b respectively. For simplicity, only the dead zone 688 and the active areas 190a and 190b of the image sensor 600 are shown (i.e., other components of the image sensor 600 are not shown).

In an embodiment, an object 730 may be positioned between the mask 720 and the image sensor 600 so that the object 730 can be imaged using the imaging system 700.

Figure 8A:
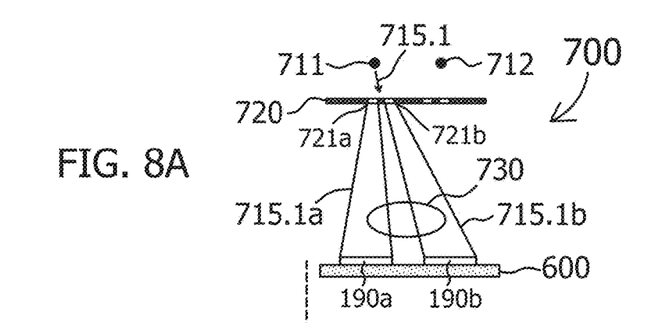

FIG. 8A shows a cross-sectional view of the imaging system 700 of FIG. 7, according to an embodiment.

First Partial Image Capture Using First Radiation Source

In an embodiment, with reference to FIG. 8A, while the imaging system 700 and the object 730 are in a first system arrangement as shown in FIG. 8A, a first partial image capture using the first radiation source 711 may be performed as follows. The second radiation source 712 may be off (i.e., not generate any radiation beam), and the first radiation source 711 may generate a radiation beam 715.1 toward the window group 721a+721b of the mask 720 resulting in 2 radiation beams 715.1a and 715.1b emitting respectively from the windows 721a and 721b and transmitting toward the object 730 and then toward the 2 active areas 190a and 190b respectively of the image sensor 600.

Using the radiation of the radiation beams 715.1a and 715.1b that has transmitted through the object 730, the image sensor 600 may capture a first partial image of the object 730.

Second Partial Image Capture Using Second Radiation Source

In an embodiment, with reference to FIG. 8B, after the first partial image of the object 730 is captured, and while the imaging system 700 and the object 730 are still in the first system arrangement, a second partial image capture using the second radiation source 712 may be performed as follows. The first radiation source 711 may be off (i.e., not generate any radiation beam), and the second radiation source 712 may generate a radiation beam 716.1 toward the window group 722a+722b of the mask 720 resulting in 2 radiation beams 716.1a and 716.1b emitting respectively from the windows 722a and 722b and transmitting toward the object 730 and then toward the 2 active areas 190a and 190b respectively of the image sensor 600.

Using the radiation of the radiation beams 716.1a and 716.1b that has transmitted through the object 730, the image sensor 600 may capture a second partial image of the object 730.

Third Partial Image Capture Using First Radiation Source

Figure 9A:
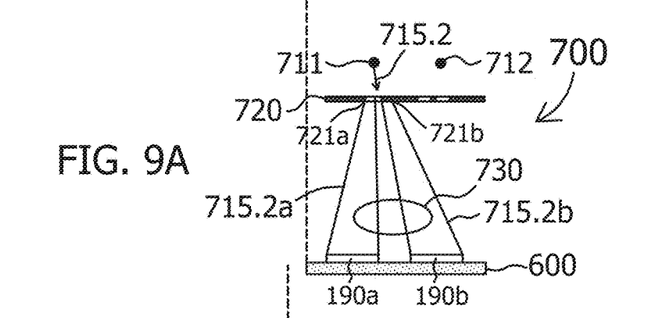

In an embodiment, with reference to FIG. 9A, after the second partial image of the object 730 is captured, a third partial image capture using the first radiation source 711 may be performed as follows. The radiation sources 711 and 712 and the object 730 may remain stationary with respect to each other, and the mask 720 and the image sensor 600 may be moved to the left with respect to the radiation sources 711 and 712 and the object 730 so that the imaging system 700 and the object 730 are in a second system arrangement as shown in FIG. 9A.

With the imaging system 700 and the object 730 being in the second system arrangement, the second radiation source 712 may be off (i.e., not generate any radiation beam), and the first radiation source 711 may generate a radiation beam 715.2 toward the window group 721a+721b of the mask 720 resulting in 2 radiation beams 715.2a and 715.2b emitting respectively from the windows 721a and 721b and transmitting toward the object 730 and then toward the 2 active areas 190a and 190b respectively of the image sensor 600.

Using the radiation of the radiation beams 715.2a and 715.2b that has transmitted through the object 730, the image sensor 600 may capture a third partial image of the object 730.

Fourth Partial Image Capture Using Second Radiation Source

Figure 9B:
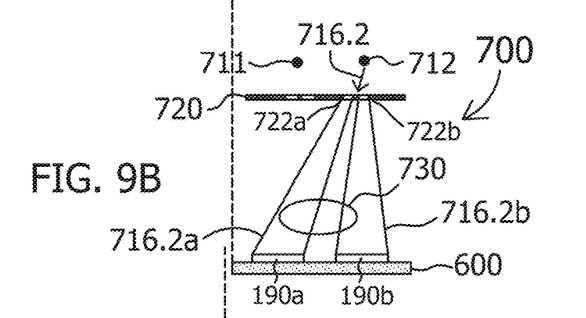

In an embodiment, with reference to FIG. 9B, after the third partial image of the object 730 is captured, and while the imaging system 700 and the object 730 are still in the second system arrangement, a fourth partial image capture using the second radiation source 712 may be performed as follows. The first radiation source 711 may be off (i.e., not generate any radiation beam), and the second radiation source 712 may generate a radiation beam 716.2 toward the window group 722a+722b of the mask 720 resulting in 2 radiation beams 716.2a and 716.2b emitting respectively from the windows 722a and 722b and transmitting toward the object 730 and then toward the 2 active areas 190a and 190b respectively of the image sensor 600.

Using the radiation of the radiation beams 716.2a and 716.2b that has transmitted through the object 730, the image sensor 600 may capture a fourth partial image of the object 730.

Fifth Partial Image Capture Using First Radiation Source

Figure 10A:
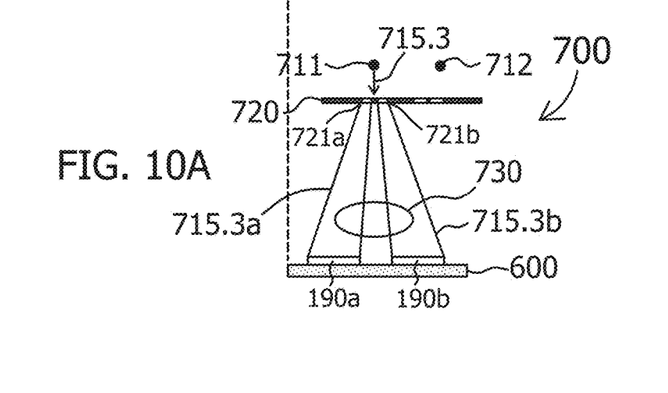

In an embodiment, with reference to FIG. 10A, after the fourth partial image of the object 730 is captured, a fifth partial image capture using the first radiation source 711 may be performed as follows. The radiation sources 711 and 712 and the object 730 may remain stationary with respect to each other, and the mask 720 and the image sensor 600 may be moved further to the left with respect to the radiation sources 711 and 712 and the object 730 so that the imaging system 700 and the object 730 are in a third system arrangement as shown in FIG. 10A.

With the imaging system 700 and the object 730 being in the third system arrangement, the second radiation source 712 may be off (i.e., not generating any radiation beam), and the first radiation source 711 may generate a radiation beam 715.3 toward the window group 721a+721b of the mask 720 resulting in 2 radiation beams 715.3a and 715.3b emitting respectively from the windows 721a and 721b and transmitting toward the object 730 and then toward the 2 active areas 190a and 190b respectively of the image sensor 600.

Using the radiation of the radiation beams 715.3a and 715.3b that has transmitted through the object 730, the image sensor 600 may capture a fifth partial image of the object 730.

Sixth Partial Image Capture Using Second Radiation Source

Figure 10B:
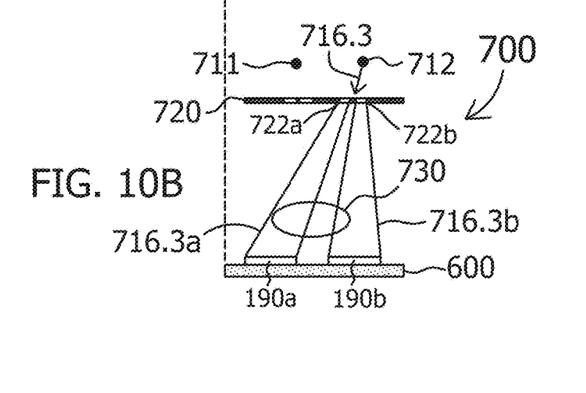

In an embodiment, with reference to FIG. 10B, after the fifth partial image of the object 730 is captured, and while the imaging system 700 and the object 730 are still in the third system arrangement, a sixth partial image capture using the second radiation source 712 may be performed as follows. The first radiation source 711 may be off (i.e., not generating any radiation beam), and the second radiation source 712 may generate a radiation beam 716.3 toward the window group 722a+722b of the mask 720 resulting in 2 radiation beams 716.3a and 716.3b emitting respectively from the windows 722a and 722b and transmitting toward the object 730 and then toward the 2 active areas 190a and 190b respectively of the image sensor 600.

Using the radiation of the radiation beams 716.3a and 716.3b that has transmitted through the object 730, the image sensor 600 may capture a sixth partial image of the object 730.

First Stitched Image

In an embodiment, after the first, third, and fifth partial images of the object 730 are captured, the first, third, and fifth partial images may be stitched resulting in a first stitched image of the object 730. In an embodiment, the stitching of the first, third, and fifth partial images may be performed by the image sensor 600.

Second Stitched Image

In an embodiment, after the second, fourth, and sixth partial images of the object 730 are captured, the second, fourth, and sixth partial images may be stitched resulting in a second stitched image of the object 730. In an embodiment, the stitching of the second, fourth, and sixth partial images may be performed by the image sensor 600.

Three-Dimensional Image of Object

In an embodiment, after the first and second stitched images of the object 730 are created, a three-dimensional image of the object 730 may be reconstructed based on the first and second stitched images of the object 730. In an embodiment, the reconstruction of the three-dimensional image of the object 730 based on the first and second stitched images of the object 730 may be performed by the image sensor 600.

Flowchart For Generalization

Figure 11:
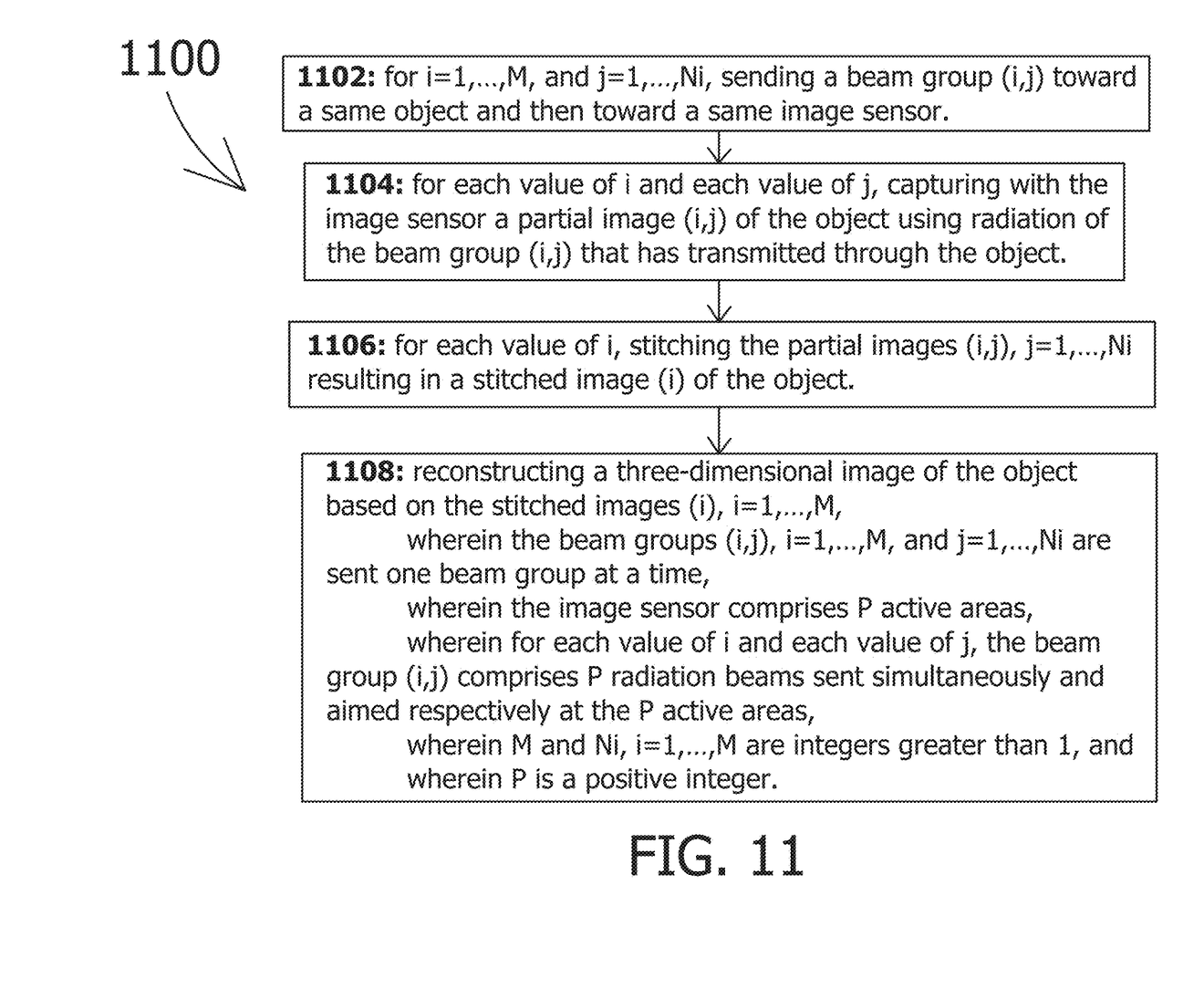
FIG. 11 shows a flowchart generalizing the operation of the imaging system.

FIG. 11 shows a flowchart 1100 generalizing the operation of the imaging system 700 described above. In step 1102, for i=1, . . . , M, and j=1, . . . , Ni, a beam group (i, j) is sent toward a same object and then toward a same image sensor.

For example, in the embodiments described above, with reference to FIG. 8A-FIG. 10B, the beam group (1,1) includes the radiation beams 715.1a and 715.1b; the beam group (1,2) includes the radiation beams 715.2a and 715.2b; the beam group (1,3) includes the radiation beams 715.3a and 715.3b; the beam group (2,1) includes the radiation beams 716.1a and 716.1b; the beam group (2,2) includes the radiation beams 716.2a and 716.2b; and the beam group (2,3) includes the radiation beams 716.3a and 716.3b. Each of these 6 beam groups is sent toward the object 730 and then toward the image sensor 600. In the embodiments described above, M=2, and N1=N2=3.

In step 1104, for each value of i and each value of j, a partial image (i, j) of the object is captured by the image sensor using radiation of the beam group (i, j) that has transmitted through the object.

For example, in the embodiments described above, with reference to FIG. 8A, the partial image (1,1) of the object 730 (i.e., the first partial image mentioned above) is captured by the image sensor 600 using the radiation of the beam group (1,1) (i.e., the radiation beams 715.1a and 715.1b) that has transmitted through the object 730.

Figure 8B:
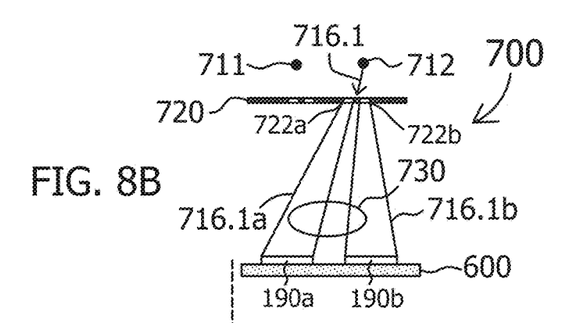

For another example, with reference to FIG. 8B, the partial image (2,1) of the object 730 (i.e., the second partial image mentioned above) is captured by the image sensor 600 using the radiation of the beam group (2,1) (i.e., the radiation beams 716.1a and 716.1b) that has transmitted through the object 730.

In step 1106, for each value of i, the partial images (i, j), j=1, . . . , Ni are stitched resulting in a stitched image (i) of the object.

For example, in the embodiments described above, for i=1, the partial images (1,1), (1,2), and (1,3) of the object 730 (i.e., the first, third, and fifth partial images respectively) are stitched resulting in a stitched image (1) of the object 730 (i.e., the first stitched image mentioned above).

For another example, for i=2, the partial images (2,1), (2,2), and (2,3) of the object 730 (i.e., the second, fourth, and sixth partial images respectively) are stitched resulting in a stitched image (2) of the object 730 (i.e., the second stitched image mentioned above).

In step 1108, a three-dimensional image of the object is reconstructed based on the stitched images (i), i=1, . . . , M. For example, in the embodiments described above, with M=2, the three-dimensional image of the object 730 is reconstructed based on the stitched images (1) and (2) (i.e., the first and second stitched images mentioned above).

In addition, in step 1108, the beam groups (i, j), i=1, . . . , M, and j=1, . . . , Ni are sent one beam group at a time. For example, in the embodiments described above, with reference to FIG. 8A-FIG. 10B, the beam group 715.1a+715.1b, the beam group 715.2a+715.2b, the beam group 715.3a+715.3b, the beam group 716.1a+716.1b, the beam group 716.2a+716.2b, and the beam group 716.3a+716.3b are sent one beam group at a time. Here, M=2, and N1=N2=3.

In addition, in step 1108, the image sensor comprises P active areas. For example, in the embodiments described above, the image sensor 600 includes P=2 active areas 190a and 190b.

In addition, in step 1108, for each value of i and each value of j, the beam group (i, j) comprises P radiation beams sent simultaneously and aimed respectively at the P active areas.

For example, in the embodiments described above, with reference to FIG. 8A, the beam group (1,1) includes P=2 radiation beams 715.1a and 715.1b which are sent simultaneously and aimed respectively at the P=2 active areas 190a and 190b.

For another example, with reference to FIG. 8B, the beam group (2,1) includes P=2 radiation beams 716.1a and 716.1b which are sent simultaneously and aimed respectively at the P=2 active areas 190a and 190b.

In addition, in step 1108, M and Ni, i=1, . . . , M are integers greater than 1, and P is a positive integer. For example, in the embodiments described above, M=2, N1=3, N2=3, and P=2.

OTHER EMBODIMENTS

Beams Are Aimed At Only Active Areas

In an embodiment, regarding step 1102 in FIG. 11, for each value of i and each value of j, no ray of the beam group (i, j) is aimed at outside the P active areas. In the embodiments described above, with reference to FIG. 8A-FIG. 10B, this feature means that each of the 6 beam groups (1,1), (1,2), (1,3), (2,1), (2,2), and (2,3) is aimed only at the P=2 active areas 190a and 190b.

For example, with reference to FIG. 8A, no ray of the beam group (1,1) (i.e., the radiation beams 715.1a and 715.1b) is aimed at outside the P=2 active areas 190a and 190b. In other words, each radiation particle of the radiation beams 715.1a and 715.1b is aimed at either the active area 190a or the active area 190b.

For another example, with reference to FIG. 8B, no ray of the beam group (2,1) (i.e., the radiation beams 716.1a and 716.1b) is aimed at outside the P=2 active areas 190a and 190b. In other words, each radiation particle of the radiation beams 716.1a and 716.1b is aimed at either the active area 190a or the active area 190b.

Each Source Scans The Entire Object

In an embodiment, regarding step 1104 in FIG. 11, for each value of i, each point of the object is in at least a partial image of the partial images (i, j), j=1, . . . , Ni. In the embodiments described above, this feature means that each of the radiation sources 711 and 712 scans the entire object 730.

For example, for i=1 (corresponding to the radiation source 711), each point of the object 730 is in at least one of the partial images (1,1), (1,2), and (1,3) of the object 730 (i.e., the first, third, and fifth partial images respectively).

For another example, for i=2 (corresponding to the radiation source 712), each point of the object 730 is in at least one of the partial images (2,1), (2,2), and (2,3) of the object 730 (i.e., the second, fourth, and sixth partial images respectively).

Radiation Beams Are Sent From Windows of Mask

In an embodiment, regarding step 1102 of FIG. 11, with reference to FIG. 8A-FIG. 10B, the P radiation beams of the beam group (i, j) are sent from respectively the P windows of the window group (i).

In the embodiments described above, the beam group (1,1) including the radiation beams 715.1a and 715.1b may be deemed being sent from respectively the windows 721a and 721b of the window group (1) of the mask 720. Similarly, the beam group (2,1) including the radiation beams 716.1a and 716.1b may be deemed being sent from respectively the windows 722a and 722b of the window group (2) of the mask 720.

Mask and Image Sensor Are Parallel

In an embodiment, the mask 720 may have a shape of a plate as shown in FIG. 7. In an embodiment, the mask 720 may be parallel to a pixel plane (not shown, but defined below) of the image sensor 600 when each of the 6 partial images (1,1), (1,2), (1,3), (2,1), (2,2), and (2,3) of the object 730 is captured. Here, the pixel plane is a plane that intersects all the pixels 150 of the image sensor 600.

Mask and Image Sensor Are of Same Distance Apart

In an embodiment, the pixel plane of the image sensor 600 and the mask 720 may be of a same distance apart when each partial image of the partial images (1,1), (1,2), (1,3), (2,1), (2,2), and (2,3) of the object 730 is captured. This is the case when the mask 720 and the pixel plane of the image sensor 600 are parallel to each other, and both of the mask 720 and the image sensor 600 move in a same scanning direction which is parallel to the mask 720 (e.g., to the left as shown in FIG. 8A-FIG. 10B).

Radiation Beams Are Truncated Pyramide Beams

In an embodiment, with reference to FIG. 8A-FIG. 10B, the radiation sources 711 and 712 may be point sources. As a result, all the 12 radiation beams of the 6 beam groups (1,1), (1,2), (1,3), (2,1), (2,2), and (2,3) are truncated pyramid beams. Specifically, the 12 radiation beams 715.1a, 715.1b, 715.2a, 715.2b, 715.3a, 715.3b, 716.1a, 716.1b, 716.2a, 716.2b, 716.3a, and 716.3b are truncated pyramid beams.

Also as a result of the radiation sources 711 and 712 being point sources, (A) all rays of the beam groups (1,1), (1,2), and (1,3) come from a point at the location of the radiation source 711, and (B) all rays of the beam groups (2,1), (2,2), and (2,3) come from a point at the location of the radiation source 712.

Radiation Sources Are On Straight Line Parallel To Image Sensor

In an embodiment, with reference to FIG. 8A-FIG. 10B, the radiation beams of each of the beam groups (1,1), (1,2), (1,3), (2,1), (2,2), and (2,3) are separate. For example, the radiation beams 715.1a and 715.1b of the beam group (1,1) are separate. As seen in FIG. 8A, no ray is part of both the radiation beams 715.1a and 715.1b. In general, multiple radiation beams are separate if no ray is part of at least two of the multiple radiation beams.

Radiation Sources Are On

In an embodiment, the radiation sources 711 and 712 may be on a straight line which is parallel to the pixel plane of the image sensor 600.

Radiation Sources By Target Bombardment

In an embodiment, the radiation source 711 may include a first metal target region (not shown) which is to be bombarded by electron beams so as to generate the radiation beams 715.1, 715.2, and 715.3 transmitting from the first metal target region toward the mask 720. Similarly, the radiation source 712 may include a second metal target region (not shown) which is to be bombarded by electron beams so as to generate the radiation beams 716.1, 716.2, and 716.3 transmitting from the second metal target region toward the mask 720.

In an embodiment, the first and second target regions may be made of copper or tungsten. In an embodiment, the radiation beams generated by the first and second target regions in response to bombardment by electron beams may be X-rays.

ALTERNATIVE EMBODIMENTS

In the embodiments described above, the partial images of the object 730 are captured in the following order: the first, second, third, fourth, fifth, and six partial images. In an alternative embodiment, the partial images of the object 730 may be captured in the following order: the first, second, fourth, third, fifth, and sixth partial images. Specifically, in this alternative embodiment, the fourth partial image is captured before the third partial image is captured.

In general, the 2 partial images for each system arrangement may be captured in any order. For example, in the third system arrangement, either the fifth partial image is captured before the sixth partial image is captured (as described above) or the sixth partial image may be captured before the fifth partial image is captured.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
   for i=1, . . . , M, and j=1, . . . , Ni, sending beam groups (i, j) toward a same object and then toward a same image sensor;
   for each value of i and each value of j, capturing with the image sensor a partial image (i, j) of the object using radiation of a beam group (i, j) that has transmitted through the object;
   for each value of i, stitching the partial images (i, j), j=1, Ni resulting in a stitched image (i) of the object; and
   reconstructing a three-dimensional image of the object based on the stitched images (i), i=1, M,
   wherein the beam groups (i, j), i=1, M, and j=1, Ni are sent one beam group at a time,
   wherein the image sensor comprises P active areas,
   wherein for each value of i and each value of j, the beam group (i, j) comprises P radiation beams sent simultaneously and aimed respectively at the P active areas,
   wherein M and Ni, i=1, M are integers greater than 1,
   wherein P is a positive integer and P >1,
   wherein the beam groups (i, j), i=1, M, and j=1, Ni are sent from a mask,
   wherein for each value of i, the beam groups (i, Ni are sent from a window group (i) of the mask,
   wherein for each value of i, the window group (i) comprises P windows,
   wherein for each value of i and each value of j, the P radiation beams of the beam group (i, j) are sent from respectively the P windows of the window group (i),
   wherein at least a pair of q and r are of 1, . . . , M,
   wherein q≠r,
   wherein at least a pair of s and t are of 1, . . . , Nq and 1, Nr respectively,
   wherein a position of the mask when the partial image (q, s) is captured and a position of the mask when the partial image (r, t) is captured are the same,
   wherein a position of the image sensor when the partial image (q, s) is captured and a position of the image sensor when the partial image (r, t) is captured are the same, and
   wherein q, s, r, t, Nq and Nr are each a positive integer.

2. The method of claim 1, wherein for each value of i and each value of j, no ray of the beam group (i, j) is aimed at outside the P active areas.

3. The method of claim 1, wherein for each value of i, each point of the object is in at least a partial image of the partial images (i, j), j=1, . . . , Ni.

4. The method of claim 1,
wherein the mask has a shape of a plate,
wherein a pixel plane intersects all sensing elements of the image sensor, and
wherein the mask is parallel to the pixel plane when each partial image of the partial images (i, j), i=1, M, and j=1, Ni is captured.

5. The method of claim 4, wherein the pixel plane and the mask is of a same distance apart when each partial image of the partial images (i, j), i=1, . . . , M, and j=1, . . . , Ni is captured.

6. The method of claim 1,
wherein for each value of i, the mask is moved in a scanning direction through Ni mask positions, and
wherein for each value of i, the partial images (i, j), j=1, Ni are captured when the mask is at the Ni mask positions respectively.

7. The method of claim 6,
wherein for each value of i, the image sensor is moved in the scanning direction through Ni image sensor positions, and
wherein for each value of i, the partial images (i, j), j=1, . . . , Ni are captured when the image sensor is at the Ni image sensor positions respectively.

8. The method of claim 1,
wherein for each value of i, all rays of the beam groups (i, j), j=1, . . . , Ni come from a point (i), and
wherein for each value of i and each value of j, each radiation beam of the beam group (i, j) is a truncated pyramid beam.

9. The method of claim 8, wherein for each value of i and each value of j, no ray is part of at least two radiation beams of the P radiation beams of the beam group (i, j).

10. The method of claim 8,
wherein the point (i), i=1, . . . , M and the object is stationary with respect to each other, and
wherein said capturing comprises moving the image sensor with respect to the object.

11. The method of claim 8, wherein the point (i), i=1, . . . , M is on a straight line parallel to a pixel plane that intersects all sensing elements of the image sensor.

12. The method of claim 8, wherein for each value of i, said sending the beam groups (i, j), j=1, . . . , Ni comprises bombarding a same metal target region at the point (i) with electron beams.

13. The method of claim 1, wherein for each value of i and each value of j, each radiation beam of the P radiation beams of the beam group (i, j) comprises X-rays.

14. A system, comprising:
an image sensor,
a mask,
wherein the system is configured to, for i=1, . . . , M, and j=1, . . . , Ni, send beam groups (i, j) through a same object and then toward the image sensor,
wherein the image sensor is configured to, for each value of i and each value of j, capture a partial image (1, j) of the object using radiation of a beam group (i, j) that has transmitted through the object,
wherein the system is configured to, for each value of i, stitch the partial images (i, j), j=1, . . . , Ni resulting in a stitched image (i) of the object,
wherein the system is configured to reconstruct a three-dimensional image of the object based on the stitched images (i), i=1, . . . , M,
wherein the beam groups (i, j), i=1, . . . , M, and j=1, . . . , Ni are sent one beam group at a time,
wherein the image sensor comprises P active areas,
wherein for each value of i and each value of j, the beam group (1, j) comprises P radiation beams sent simultaneously and aimed respectively at the P active areas,
wherein M and Ni, i=1, . . . , M are integers greater than 1,
wherein P is a positive integer and P >1;
wherein the beam groups (i, j), i=1, . . . , M, and j=1, . . . , Ni are sent from the mask,
wherein for each value of i, the beam groups (i, j), j=1, . . . , Ni are sent from a window group (i) of the mask,
wherein for each value of i, the window group (i) comprises P windows,
wherein for each value of i and each value of j, the P radiation beams of the beam group (i, j) are sent from respectively the P windows of the window group (i),
wherein at least a pair of q and r are of 1, . . . , M,
wherein q≠r,
wherein at least a pair of s and t are of 1, . . . , Nq and 1, . . . , Nr respectively,
wherein a position of the mask when the partial image (q, s) is captured and a position of the mask when the partial image (r, t) is captured are the same,
wherein a position of the image sensor when the partial image (q, s) is captured and a position of the image sensor when the partial image (r, t) is captured are the same, and
wherein q, s, r, t, Nq and Nr are each a positive integer.

15. The system of claim 14, wherein for each value of i and each value of j, no ray of the beam group (i, j) is aimed at outside the P active areas.

16. The system of claim 14, wherein for each value of i, each point of the object is in at least a partial image of the partial images (i, j), j=1, . . . , Ni.

17. The system of claim 14,
wherein the mask has a shape of a plate,
wherein a pixel plane intersects all sensing elements of the image sensor, and
wherein the mask is parallel to the pixel plane when each partial image of the partial images (i, j),1=1, M, and j=1, Ni is captured.

18. The system of claim 17, wherein the pixel plane and the mask is of a same distance apart when each partial image of the partial images (i, j), i=1, . . . , M, and j=1, . . . , Ni is captured.

19. The system of claim 14,
wherein for each value of i, the mask is configured to move in a scanning direction through Ni mask positions, and
wherein for each value of i, the partial images (i, j), j=1, Ni are captured when the mask is at the Ni mask positions respectively.

20. The system of claim 19,
wherein for each value of i, the image sensor is configured to move in the scanning direction through Ni image sensor positions, and
wherein for each value of i, the partial images (i, j), j=1, . . . , Ni are captured when the image sensor is at the Ni image sensor positions respectively.

21. The system of claim 14,
wherein for each value of i, all rays of the beam groups (i, j), j=1, . . . , Ni come from a point (i), and
wherein for each value of i and each value ofj, each radiation beam of the beam group (i, j) is a truncated pyramid beam.

22. The system of claim 21, wherein for each value of i and each value ofj, no ray is part of at least two radiation beams of the P radiation beams of the beam group (i, j).

23. The system of claim 21,
wherein the point (i), i=1, . . . , M and the object is stationary with respect to each other, and
wherein the image sensor is configured to move with respect to the object.

24. The system of claim 21, wherein the point (i), i=1, . . . , M is on a straight line parallel to a pixel plane that intersects all sensing elements of the image sensor.

25. The system of claim 21, wherein the system is configured to, for each value of i, bombard a metal target region at the point (i) with electron beams.

26. The system of claim 14, wherein for each value of i and each value of j, each radiation beam of the P radiation beams of the beam group (i, j) comprises X-rays.

* * * * *